(12) United States Patent
Culler et al.

(10) Patent No.: US 7,084,117 B2
(45) Date of Patent: Aug. 1, 2006

(54) PHARMACEUTICAL COMPOSITIONS WHICH INHIBIT VASCULAR PROLIFERATION AND METHOD OF USE THEREOF

(75) Inventors: Michael Dewitt Culler, Hopkinton, MA (US); Romano Danesi, Leghorn (IT); Guido Bocci, Lucca (IT); Mario Deltacca, Pisa (IT)

(73) Assignee: Societe de Conseils de Recherches et d'Applications Scientifiques, SAS, Paris (FR)

( * ) Notice: Subject to any disclaimer, the term of this patent is extended or adjusted under 35 U.S.C. 154(b) by 0 days.

(21) Appl. No.: 10/466,152

(22) PCT Filed: Jan. 14, 2002

(86) PCT No.: PCT/US02/01125

§ 371 (c)(1),
(2), (4) Date: Nov. 18, 2003

(87) PCT Pub. No.: WO02/064160

PCT Pub. Date: Aug. 22, 2002

(65) Prior Publication Data

US 2004/0082517 A1     Apr. 29, 2004

Related U.S. Application Data

(60) Provisional application No. 60/275,294, filed on Mar. 13, 2001, provisional application No. 60/261,439, filed on Jan. 12, 2001.

(51) Int. Cl.
*A61K 38/31* (2006.01)
(52) U.S. Cl. ............................. 514/11; 514/16; 530/311
(58) Field of Classification Search .................. 514/11, 514/16, 414; 530/311; 548/468
See application file for complete search history.

(56) References Cited

U.S. PATENT DOCUMENTS 5,750,499 A * 5/1998 Hoeger et al. .................. 514/9
5,912,247 A * 6/1999 Jinbo et al. .................... 514/23
6,060,275 A * 5/2000 Hacohen et al. ............ 435/69.1
6,903,074 B1 * 6/2005 Morgan et al. ................ 514/15
2002/0103526 A1 * 8/2002 Steinke ...................... 623/1.11

FOREIGN PATENT DOCUMENTS

| WO | 96/07398 | 3/1996 |
|---|---|---|
| WO | 99/049884 | 10/1999 |
| WO | 99/056769 | 11/1999 |
| WO | 99/065508 | 12/1999 |
| WO | 00/12111 B | 3/2000 |
| WO | WO 00/10552 A2 * | 3/2000 |

OTHER PUBLICATIONS

Albini et al. Somatostatin controls Kaposi's sarcoma tumor growth through inhibition of angiogenesis. FASEB Journal. 1999, vol. 13, pp. 647-655.*
Antonian et al. Biotransformations Of The Anti-Angiogenic Compound SU5416. Drug Metabolism And Disposition. 2000, vol. 28, No. 12, pp. 1505-1512.*
Vajkoczy et al. Inhibition of Tumor Growth, Angiogenesis . . . Neoplasia. Apr. 1999, vol. 1, No. 1, pp. 31-41.*
Mccombe, M. et al., "Effect of a Long-acting Somatostatin Analogue (BIM23104) on Proliferative Diabetic Retinopathy: A Pilot Study," Eye, 1991, 5(5):569-575.
Aavik, E. et al., "Elimination of Vascular Fibrointimal Hyperplasia by somatostatin receptor," FASEB, 2002, 16(7):2002-2005.
Barrie, R. et al., "Inhibition of Angiogenisis by Somatostatin and Somatostatin-like Compounds is Structurally Dependent," J. of Surgical Research, 1993, 4(55):446-450.
Patel, Y.C., "Somatostatin and its receptor family", Frontiers in Neuroendocrinology, 1999, 20:157-198.
Lapinski, et al., "Development of a selective agonist at the somatostatin receptor subtype SSTR1", J. Pharm. Exper. Therap., 1996, 276:1089-1094.

* cited by examiner

*Primary Examiner*—Jeffrey Edwin Russel
(74) *Attorney, Agent, or Firm*—Yankwich & Associates; Brian R. Morrill; Alan F. Feeney

(57) ABSTRACT

The present invention relates to a method of treating vascular proliferation in a patient in need thereof. The method includes the step of administering a therapeutically effective amount of a type-1 somatostatin agonist to said patient.

12 Claims, 8 Drawing Sheets

Figure 1. Treatment protocol of HEMC-1 cells

Figure 2. Treatment protocol of placental vessel explants

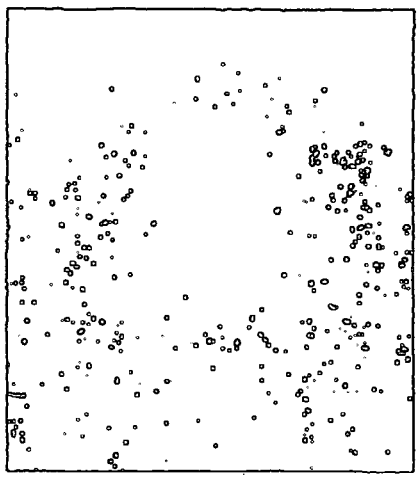
Figure 8. BIM23014C $10^{-6}$ M
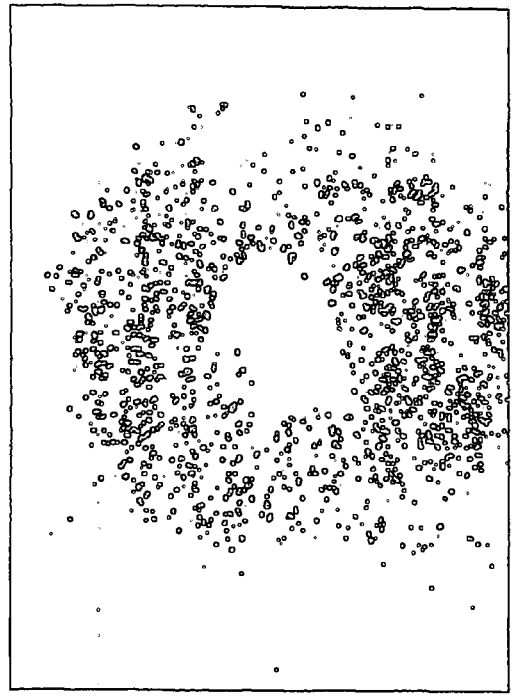
Figure 10. BIM23190C $10^{-9}$ M
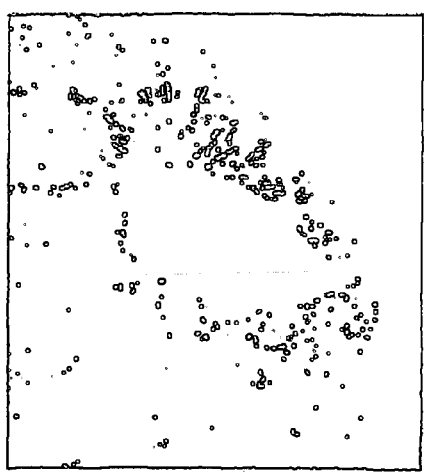
Figure 7. SMS-14 $10^{-7}$ M
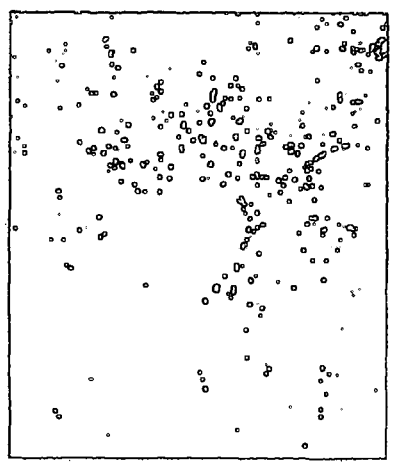
Figure 9. BIM23745C $10^{-8}$ M

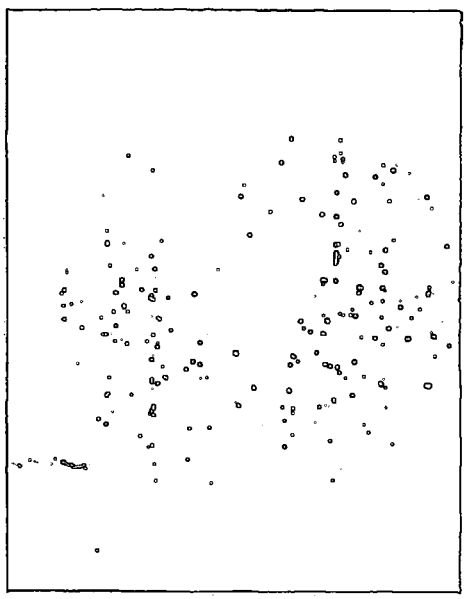
Figure 12. BIM23208C $10^{-8}$ M
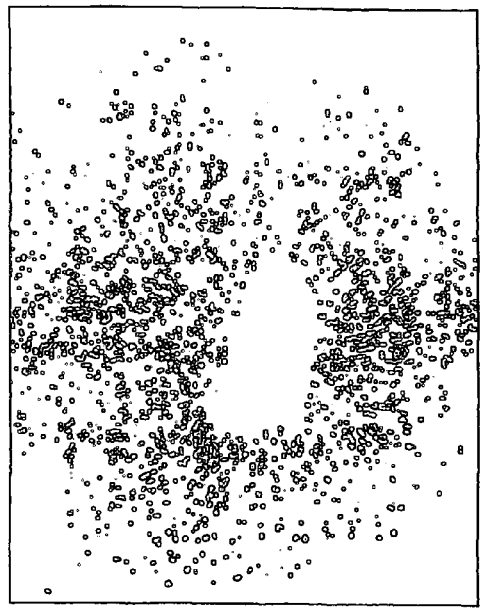
Figure 14. BIM23120C $10^{-9}$ M
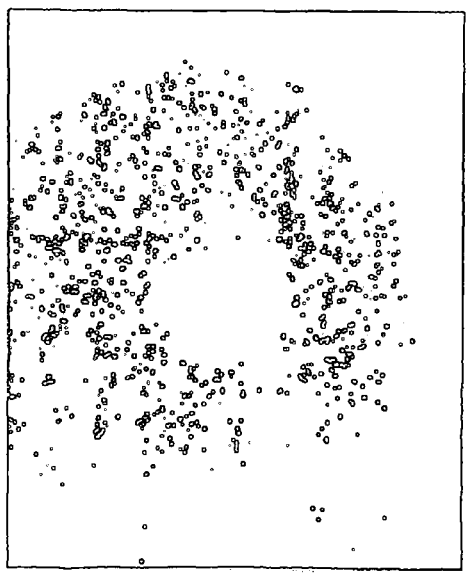
Figure 11. BIM23268C $10^{-7}$ M
Figure 13. BIM23197C $10^{-7}$ M

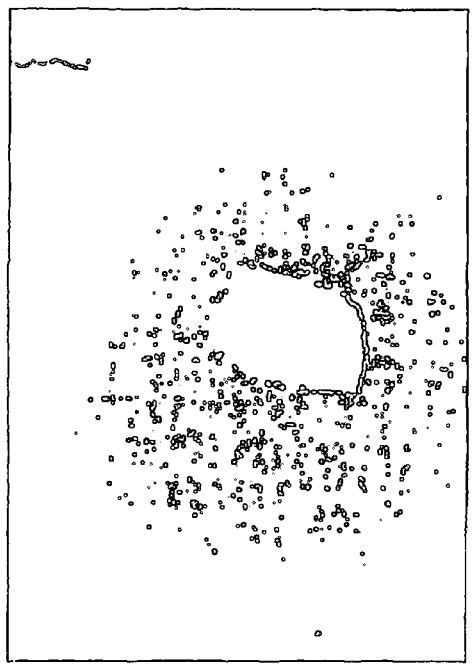
Figure 15. BIM23926C $10^{-7}$ M
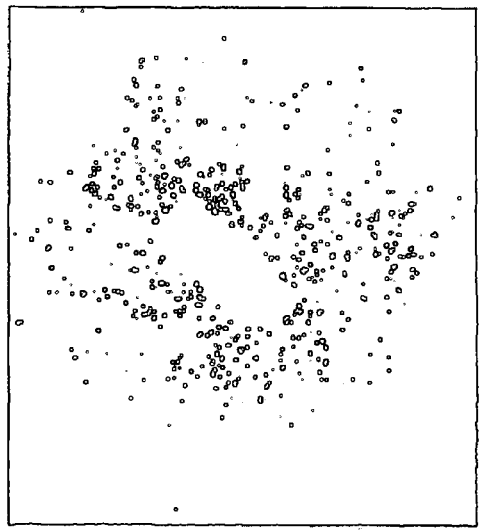
Figure 16. SU5416 $10^{-6}$ M Table 1  Proliferation of HEMC-1 human endothelial cells in vitro

| Concentration | BIM-23120C | | BIM-23197C | | BIM-23205C | | BIM-23190C | | BIM-23268C | | BIM-23745C | | BIM-23014C | | BIM-23926C | | SMS-14 | |
|---|---|---|---|---|---|---|---|---|---|---|---|---|---|---|---|---|---|---|
| | % of controls | | % of controls | | % of controls | | % of controls | | % of controls | | % of controls | | % of controls | | % of controls | | % of controls | |
| 0 M | 100 | | 100 | | 100 | | 100 | | 100 | | 100 | | 100 | | 100 | | 100 | |
| $10^{-6}$ M | 103.97±2.07 | | 87.61±3.6 | | 122.58±7.3 | | 113.55±6.5 | | 118.06±8.2 | | 40.0±2.0 | | 80.0±3.2 | | 56.78±4.9 | | 73.3±4.1 | |
| $10^{-7}$ M | 74.27±4.5 | | 78.25±2.5 | | 81.29±3.2 | | 92.26±3.1 | | 87.74±3.7 | | 46.55±2.3 | | 51.2±4.7 | | 55.33±3.3 | | 71.25±2.1 | |
| $10^{-8}$ M | 88.01±3.7 | | 73.39±2.1 | | 68.38±3.9 | | 60.0±2.2 | | 111.61±2.5 | | 49.7±1.9 | | 65.05±3.1 | | 65.54±3.5 | | 69.7±2.5 | |
| $10^{-9}$ M | 102.39±5.2 | | 83.96±3.2 | | 77.42±4.0 | | 87.74±2.5 | | 94.19±4.2 | | 56.79±2.7 | | 78.0±2.7 | | 79.95±4.6 | | 77.85±3.3 | |
| $10^{-10}$ M | 86.57±9.8 | | | | | | | | | | | | | | 88.10±5.3 | | | |

Treatment was delivered on day 1, 24 hours after plating and repeated 48 hours later; cell count was performed after additional 24 hours. SMS-14 was added on each day. SU5416 was added at 10-6 M to culture media of separate wells and resulted in 43.85 ±3.02 % survival as compared to untreated controls.

Table II  Proliferation of endothelial cells from blood vessels explanted from human placenta

| Concentration | BIM-23120C | BIM-23197C | BIM-23205C | BIM-23190C | BIM-23268C | BIM-23745C | BIM-23014C | BIM-23926C | SMS-14 |
|---|---|---|---|---|---|---|---|---|---|
| | % of controls | % of controls | % of controls | % of controls | % of controls | % of controls | % of controls | % of controls | % of controls |
| 0 M | 100 | 100 | 100 | 100 | 100 | 100 | 100 | 100 | 100 |
| $10^{-6}$ M | 105.6±10.2 | 98.99±8.7 | 93.08±7.8 | 107.98±8.5 | 98.14±10.7 | 70.75±7.5 | 73.66±8.7 | 38.39±10.6 | 73.25±7.5 |
| $10^{-7}$ M | 94.78±8.4 | 62.72±7.9 | 83.77±10.2 | 102.39±7.3 | 81.12±11.6 | 62.99±8.2 | 79.01±8.2 | 17.18±11.8 | 44.03±5.2 |
| $10^{-8}$ M | 88.18±11.3 | 71.54±8.2 | 72.07±8.5 | 95.12±10.7 | 84.31±12.1 | 42.84±5.6 | 80.24±10.1 | 41.54±7.9 | 68.72±5.4 |
| $10^{-9}$ M | 78.76±7.6 | 114.23±7.6 | 97.87±10.9 | 91.75±10.9 | 86.97±8.4 | 63.41±6.8 | 90.53±11.3 | 55.94±13.6 | 84.77±7.1 |
| $10^{-10}$ M | 86.57±9.8 | 126.65±11.2 | 105.32±11.3 | 103.98±12 | 76.33±7.6 | 82.43±8.5 | 90.94±12.6 | 62.32±12 | 99.18±7. |

Treatments were delivered every other day over a 28-day period. SU5416 was added every two days at 10-6 M culture media of separate explants and resulted in 32.92 ±9.7% of SI as compared to untreated controls

Figure 17

PHARMACEUTICAL COMPOSITIONS WHICH INHIBIT VASCULAR PROLIFERATION AND METHOD OF USE THEREOF

CROSS REFERENCE TO RELATED APPLICATIONS

This application is the National Stage of International Application No. PCT/US02/01125, filed Jan. 14, 2002, which was published in English under PCT Article 21(2), which claims benefit of United States Provisional Application Nos. 60/261,439 filed Jan. 12, 2001 and 60/275,294 filed Mar. 13, 2001.

BACKGROUND OF THE INVENTION

Angiogenesis, the development of new capillaries from preexisting blood vessels, is a critical process in the progression of solid neoplasms and in many other pathological conditions such as diabetic retinopathy and rheumatoid arthritis (Folkman, J., Nature Medicine 1995, 1: 27–31). Different strategies to target the vascular development have been extensively studied and the availability of reliable in vitro model systems in model systems in angiogenesis research has been crucial for the study of specific inhibitors (Jain, R. K., et al., Nature Medicine 1997, 3: 1203–1208).

It is now widely recognized that the ability of a tumor to induce proliferation of new blood vessels from its host has a profound effect on cancer growth and metastasis. The process of tumor angiogenesis is mediated by a balance of positive and negative regulators of microvessel growth and the development of new blood vessels may be divided into three different sequential steps: 1) cell-mediated, proteolytic degradation of the basement membrane; 2) endothelial cell migration and proliferation out of the vessel into the surrounding extracellular matrix; 3) organization of the cells into tube-like structures (Folkman, J., Nature Medicine 1995, 1: 27–31).

Somatostatin (somatotropin release inhibiting factor or SRIF) has both a 14 amino acid isoform (somatostatin-14) and a 28 amino acid isoform (somatostatin-28). See Wilson, J. & Foster, D., *Williams Textbook of Endocrinology*, p. 510 (7th ed., 1985). The compound is an inhibitor of secretion of the growth hormone and was originally isolated from the hypothalamus. Brazeau, et al., Science 179:77 (1973). Native somatostatin has a very short duration of effect in vivo since it is rapidly inactivated by endo- and exopeptidase. Many novel analogs (e.g., peptide and non-peptide compounds) have been prepared in order to enhance the duration of effect, biological activity, and selectivity (e.g., for the particular somatostatin receptor) of this hormone. Such analogs of somatostatin will be called "somatostatin agonists" herein.

Various somatostatin receptors (SSTRs) have been isolated, e.g., SSTR-1, SSTR-2, SSTR-3, SSTR-4, and SSTR-5. Thus, a somatostatin agonist may be a SSTR-1 agonist, and/or a SSTR-2 agonist, and/or a SSTR-3 agonist, and/or a SSTR-4 agonist and/or a SSTR-5 agonist.

The antiangiogenic activity of somatostatin analogues has been previously demonstrated in some in vitro and in vivo experimental models (Danesi, R. et al., Clinical Cancer Research 1997, 3: 265–272; Woltering, E. A., et al., Investigational New Drug 1997, 15: 77–86). In addition to this, long-term octreotide treatment was able to reduce the progression of neovascularization associated with severe proliferative retinopathy in diabetic patients (Mallet et al., 1992).

The determination of which somatostatin subtype or subtypes are involved in the antiangiogenic property of somatostatin would allow for the development of therapeutic compositions with maximum efficacy and minimum side effects. However, previous studies in this field have resulted in contradictory and/or inconclusive findings regarding the role which each of the five somatostatin receptor subtypes may play in respect of the antiangiogenic activity of somatostatin.

SUMMARY OF THE INVENTION

The present invention relates to compositions comprising a somatostatin type-1 receptor agonist which are useful for the inhibition of vascular proliferation in a subject. The present invention further relates to a method of treating vascular proliferation, e.g., angiogenesis and restenosis, in a patient (e.g., a mammal such as a human) in need of such treatment. The method includes the step of administering a therapeutically effective amount of a somatostatin type-1 receptor (SSTR-1) agonist (e.g., a somatostatin type-1 selective agonist) to said patient.

The present invention also relates to a method of inhibiting smooth muscle proliferation, endothelial cell proliferation, and new blood vessel sprouting in a patient in need of such inhibition. The method includes the step of administering a therapeutically effective amount of a somatostatin type-1 receptor (SSTR-1) agonist (e.g., a somatostatin type-1 selective agonist) to said patient.

Examples of clinical indications which can be treated by the present invention include, but are not limited to, autoimmune diseases (e.g., arthritis, scleroderma, etc.), cancerous tumors, corneal graft neovascularization, diabetic retinopathy, hemangioma, hypertrophic scars, and psoriasis, as well as vascular proliferation associated with surgical procedures, e.g., angioplasty and AV shunts.

Further examples of disease states that may be amenable to treatment with the subject therapeutic composition and method of the invention are, in respect of the skin: warts, granulomas, Kaposi's sarcoma, allergic oedema, and the like; in respect to the uterus and ovary: endometriosis, dysfunctional uterine bleeding, follicular cysts, and the like; in respect of the eye: retinopathy of prematurity, choroidal and other intraocular disorders, macular degeneration, age-related macular degeneration, and the like.

Further examples of disease states that may be amenable to treatment with the subject therapeutic composition and method of the invention are disclosed in Folkman, J., Seminars in Medicine of the Beth Israel Hospital, Boston, Vol. 333, No 26, pp. 1757–1763.

Indeed as is well known in the art the list of known diseases and conditions for which an agent capable of inhibiting angiogenesis, smooth muscle proliferation, endothelial cell proliferation, and/or new blood vessel sprouting is quite substantial, and includes, without limitation: solid tumors, tumor metastasis, benign tumors, for example, acoustic neuromas, neurofibromas, and trachomas, leukemia, pyogenic granuloma, myocardial angiogenesis, plaque neovascularization, atherosclerosis, coronary collaterals, cerebral collaterals, arteriovenous malformations, ischemic limb angiogenesis, ocular and corneal angiogenic conditions, for example, corneal graft rejection, Osler-Webber Syndrome, rubeosis, neovascular glaucoma, retrolental fibroplasia, and diabetic retinopathy, diabetic neovascularization, wound healing, fractures, vasculogenesis, hematopoiesis, ovulation, menstruation, placentation, cat scratch disease (Rochele minalia quintosa), ulcers (peptic; Helicobacter pylori), psoriasis, (including, e.g., telangiectasia psoriasis), rheumatoid arthritis, Crohn's disease, intestinal adhesions, scarring, (i.e., formation of high density tissue including cells and connective tissue), hypertrophic scars, (i.e., keloids), telangiectasia; hemophiliac joints; angiofibroma; and wound granulation. These diseases and conditions are discussed in detail in the literature, for example, as in the following U.S. patents and International Patent Publications.: U.S. Pat. Nos. 6,323,228, 6,294,532, 6,288,228, 6,288,024, 6,284,726, 6,280,739, 6,265,407, 6,265,403, 6,258,812, 6,255,355, 6,255,353, 6,251,867, 6,242,481, 6,235,756, 6,235,741, 6,228,879, 6,228,871, 6,225,340, 6,214,800, 6,201,104, 6,177,401, 6,174,861, 6,150,407, 6,150,362, 6,117,862, 6,114,355, 6,090,794, 6,086,865, 6,071,948, 6,057,290, 6,057,122, 6,028,061, 6,025,353, 6,025,331, 6,024,688, 6,017,949, 5,997,868, 5,994,388, 5,994,292, 5,990,280, 5,985,878, 5,985,330, 5,981,484, 5,972,922, 5,972,896, 5,948,403, 5,932,611, 5,902,790, 5,874,081, 5,847,002, 5,843,925, 5,837,680, 5,807,731, 5,801,146, 5,766,591, 5,753,230, 5,744,492, 5,733,876, 5,721,226, 5,712,291, 5,698,586, 5,696,147, 5,677,181, 5,646,136, 5,629,340, 5,629,327, 5,610,166, 5,593,990, 5,574,026, 5,567,693, 5,567,417, 5,563,130, 5,512,550, 5,506,208, WO02/02609, WO02/02593, WO02/00877, WO02/00690, WO02/00017, WO01/93806, WO01/85796, WO01/81579, WO01/81311, WO01/79157, WO01/74299, WO01/72699, WO01/72297, WO01/66127, WO01/62799, WO01/62725, WO01/59100, WO01/58899, WO01/51048, WO01/46110, WO01/45751, WO01/35977, WO01/34195, WO01/29085, WO01/28577, WO01/25433, WO01/23375, WO01/21831, WO01/19987, WO01/19868, WO01/12809, WO01/12226, WO01/12210, WO01/10859, WO01/09113, WO01/07057, WO01/04157, WO01/03720, WO01/00201, WO00/75124, WO00/73445, WO00/73340, WO00/59532, WO00/54770, WO00/54762, WO00/53757, WO00/53753, WO00/53752, WO00/52158, WO00/48591, WO00/47212, WO00/47193, WO00/43393, WO00/40597, WO00/35407, WO00/32221, WO00/32180, WO00/30628, WO00/27866, WO00/27415, WO00/27340, WO00/24415, WO00/21561, WO00/20577, WO00/20026, WO00/19995, WO00/15792, WO00/12089, WO00/10507, WO00/10506, WO00/09657, WO00/09495, WO00/05356, WO00/02902, WO00/02871, WO00/02585, WO00/01383, WO99/62549, WO99/61590, WO99/61432, WO99/60984, WO99/58139, WO99/48495, WO99/45909, WO99/37776, WO99/31088, WO99/26622, WO99/26480, WO99/23105, WO99/22760, WO99/16755, WO99/16465, WO99/14234, WO99/10349, WO99/09982, WO99/04806, WO99/04803, WO98/58929, WO98/58919, WO98/54093, WO98/51326, WO98/41205, WO98/36760, WO98/35958, WO98/31688, WO98/19712, WO98/19649, WO98/17796, WO98/13071, WO98/12226, WO98/05323, WO98/05293, WO97/45137, WO97/41824, WO97/35567, WO97/32583, WO97/30085, and WO97/26258. The contents of each of the foregoing patents and patent publications is hereby incorporated by reference in its entirety.

Definitions of "somatostatin type-1 receptor agonist" and "somatostatin type-1 receptor selective agonist" are provided below. A therapeutically effective amount depends upon the condition being treated, the route of administration chosen, and the specific activity of the compound used and ultimately will be decided by the attending physician or veterinarian (e.g., between 5 g/day and 5 mg/day). In one embodiment, the somatostatin agonist is administered to the patient until the condition being treated has subsided. In another embodiment, the somatostatin agonist is administered for the lifetime of the patient.

The somatostatin agonist may be injected parenterally, e.g., intravenously, into the bloodstream of the subject being treated. However, it will be readily appreciated by those skilled in the art that the route, such as intravenous, subcutaneous, intramuscular, intraperitoneal, enterally, transdermally, transmucously, sustained released polymer compositions (e.g., a lactic acid polymer or lactic acid and glycolic acid copolymer microparticle or implant), profusion, nasal, oral, etc., will vary with the condition being treated and the activity and bioavailability of the somatostatin agonist being used.

The somatostatin agonist may also be provided as a coating or as a component of a coating on a surface of a device implanted within the body. For example, the provision of the somatostatin agonist within or upon a vascular stent is useful for the treatment of restenosis which is often associated with stent implantation.

The SSTR-1 agonist can be administered systemically and/or locally or topically, as needed. For prevention of adhesions, the SSTR-1 agonist would typically be applied at the time of surgery, preferably in a controlled release formulation and/or using barrier technology.

While it is possible for the somatostatin agonist to be administered as the pure or substantially pure compound, it may also be presented as a pharmaceutical formulation or preparation. The formulations to be used in the present invention, for both humans and animals, comprise any of the somatostatin agonists to be described below, together with one or more pharmaceutically acceptable carriers thereof, and optionally other therapeutic ingredients.

The carrier must be "acceptable" in the sense of being compatible with the active ingredient(s) of the formulation (e.g., capable of stabilizing peptides) and not deleterious to the subject to be treated. Desirably, the formulation should not include oxidizing agents or other substances with which peptides are known to be incompatible. For example, somatostatin agonists in the cyclized form (e.g., internal cysteine disulfide bond) can be oxidized; thus, the presence of reducing agents as excipients could lead to an opening of the cysteine disulfide bridge. On the other hand, highly oxidative conditions can lead to the formation of cysteine sulfoxide and to the oxidation of tryptophane. Consequently, it is important to carefully select the excipient. pH is another key factor, and it may be necessary to buffer the product under slightly acidic conditions (pH 5 to 6).

The formulations may conveniently be presented in unit dosage form and may be prepared by any of the methods well known in the art of pharmacy. All methods include the step of bringing the active ingredient(s) into association with the carrier which constitutes one or more accessory ingredients.

In general, the formulations for tablets or powders are prepared by uniformly and intimately blending the active ingredient with finely divided solid carriers, and then, if necessary, as in the case of tablets, forming the product into the desired shape and size.

Formulations suitable for parenteral (e.g., intravenous) administration, on the other hand, conveniently comprise sterile aqueous solutions of the active ingredient(s). Preferably, the solutions are isotonic with the blood of the subject to be treated. Such formulations may be conveniently prepared by dissolving solid active ingredient(s) in water to produce an aqueous solution, and rendering said solution sterile. The formulation may be presented in unit or multidose containers, for example, sealed ampoules or vials.

Formulations suitable for sustained release parenteral administrations (e.g., biodegradable polymer formulations such as polyesters containing lactic or glycolic acid residues) are also well known in the art. See, e.g., U.S. Pat. Nos. 3,773,919 and 4,767,628 and PCT Publication No. WO 94/15587.

Methods and formulations for the treatment and/or coating of surgical stents, wherein said coating may comprise a pharmaceutically active compound, are also well known in the art. See, e.g., U.S. Pat. Nos. 6,214,115, 6,090,901 and 6,083,257, and International Patent Publication No.'s WO O1/01957 and WO 00/02599.

The somatostatin or somatostatin agonist may also be administered with another compound capable of lowering blood levels of triglycerides, cholesterol, or glycerol, such as fibrates (e.g., bezafibrate, gemfibrozil, and clofibrate), HMG-COA reductase inhibitors (e.g., pravastatin, simvastatin, and fluorastatin, Atorvastatin, and Lovastatin), bile acid binding resins (e.g., cholestyramine and colestipol), nicotinic acid compounds (e.g., nicotinic acid and niceritrol), and fish oils. See Workshop Treatment of Hyperlipidemia 1996–2 (Lakemedelsverket, Uppsala, Sweden, 1996).

Other features and advantages of the invention will be apparent from the following description of the preferred embodiments and from the claims.

BRIEF DESCRIPTION OF THE DRAWINGS

FIG. 7 is a view of a culture treated with SMS-14 $10^{-7}$ M;

FIG. 8 is a view of a culture treated with BIM23014C $10^{-6}$ M;

FIG. 9 is a view of a culture treated with BIM23745C $10^{-8}$ M;

FIG. 10 is a view of a culture treated with BIM23190C $10^{-9}$ M;

FIG. 11 is a view of a culture treated with BIM23268C $10^{-7}$ M;

FIG. 12 is a view of a culture treated with BIM23206C $10^{-8}$ M;

FIG. 13 is a view of a culture treated with BIM23197C $10^{-7}$ M;

FIG. 14 is a view of a culture treated with BIM23120C $10^{-9}$ M;

FIG. 15 is a view of a culture treated with BIM23926C $10^{-7}$ M;

FIG. 16 is a view of a culture treated with SU5416 $10^{-6}$ M; and

FIG 17 consists of two Tables one of which reports the results of the cytotoxicity assay (Table I) and the other reports data compiled on the activity of selective somatostatin analogues on capillaries sprouts (Table II).

DETAILED DESCRIPTION OF THE INVENTION

Figure 1:
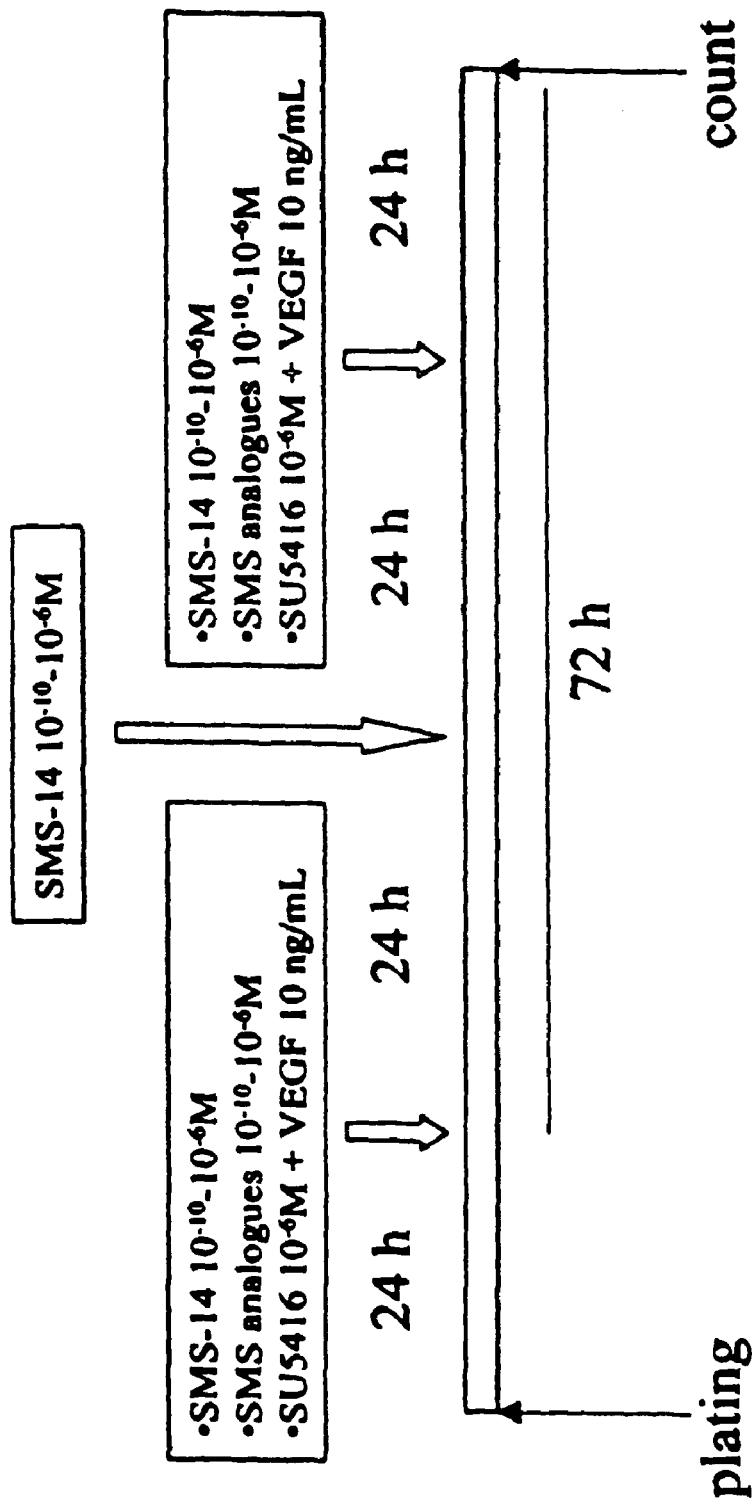
FIG. 1 is a schematic of the treatment protocol discussed at page 13, lines 7–12.

It is believed that one skilled in the art can, based on the description herein, utilize the present invention to its fullest extent. The following specific embodiments are, therefore, to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

What is meant by a somatostatin type-1 receptor agonist (i.e., SSTR-1 agonist) is a compound which (1) has a high binding affinity (e.g., Ki of less than 1000 nM or preferably less than 100 nm or less than 10 nM) for SSTR-1 (e.g., as defined by the receptor binding assay described below) and (2) decreases the rate or extent of vascular proliferation, (e.g., as shown by the biological assay described below).

What is meant by a somatostatin type-1 receptor selective agonist is a somatostatin agonist which (1) has a higher binding affinity (i.e., Ki) for SSTR-1 than for either SSTR-2, SSTR-3, SSTR-4 or SSTR-5, (e.g., as defined by the receptor binding assay described below) and (2) decreases the rate or extent of vascular proliferation, (e.g., as shown by the biological assay described below).

In one embodiment, the somatostatin type-1 receptor selective agonist is also a SSTR-1 agonist.

Examples of somatostatin agonists are those covered by formulae or those specifically recited in the publications set forth below, all of which are hereby incorporated by reference.

Van Binst, G. et al. Peptide Research 5:8 (1992);

Horvath, A. et al. Abstract, "Conformations of Somatostatin Analogs Having Antitumor Activity", 22nd European peptide Symposium, Sep. 13–19, 1992, Interlaken, Switzerland;

Curtis et al., Am. J. Physiol. Heart. Circ. Physiol, 278: H1815 (2000);

Nicolaou et al., Design and synthesis of a peptidomimetic employing β-D-glucose for scaffolding, in Peptides, Rivier and Marshall, eds., ESCOM (1990), Papageorgiou et al., "Design, synthesis, and binding affinity of a non peptide mimic of somatostatin" Bioorganic & Medicinal Chemistry Letters, vol. 2, pp. 135–140, 1992; and R. Hirschmann et al. "De novo design and synthesis of somatostatin non-peptide peptidomimetics utilizing beta-D-glucose as a novel scaffolding, J. Am. Chem. Soc., vol. 115, pp. 12550–12568, 1993.

PCT Application No. WO 91/09056 (1991);

EP Application No. 0 363 589 A2 (1990);

EP Application No. P5 164 EU (Inventor: G. Keri);

U.S. Pat. No. 6,262,229

U.S. Pat. No. 6,197,963

U.S. Pat. No. 6,159,941

U.S. Pat. No. 6,127,343

U.S. Pat. No. 6,083,960
U.S. Pat. No. 6,020,349
U.S. Pat. No. 5,552,534
U.S. Pat. No. 5,817,879

H-D-Phe-Phe-Phe-D-Trp-Lys-Thr-Phe-Thr-NH$_2$;
H-Cys-Phe-Phe-D-Trp-Lys-Ser-Phe-Cys-NH$_2$;
H-Cys-Phe-Tyr-D-Trp-Lys-Thr-Phe-Cys-NH$_2$;
H-Cys-Phe-Tyr(I)-D-Trp-Lys-Thr-Phe-Cys-NH$_2$;

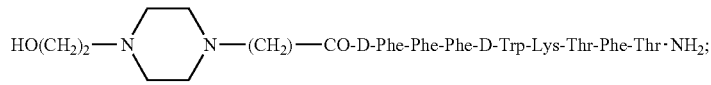

U.S. Pat. No. 5,811,512
U.S. Pat. No. 4,904,642 (1990);
U.S. Pat. No. 4,871,717 (1989);
U.S. Pat. No. 4,853,371 (1989);
U.S. Pat. No. 4,725,577 (1988);
U.S. Pat. No. 4,684,620 (1987);
U.S. Pat. No. 4,650,787 (1987);
U.S. Pat. No. 4,603,120 (1986);
U.S. Pat. No. 4,585,755 (1986);
EP Application No. 0 203 031 A2 (1986);
U.S. Pat. No. 4,522,813 (1985);
U.S. Pat. No. 4,486,415 (1984);
U.S. Pat. No. 4,485,101 (1984);
U.S. Pat. No. 4,435,385 (1984);
U.S. Pat. No. 4,395,403 (1983);
U.S. Pat. No. 4,369,179 (1983);
U.S. Pat. No. 4,360,516 (1982);
U.S. Pat. No. 4,358,439 (1982);
U.S. Pat. No. 4,328,214 (1982);
U.S. Pat. No. 4,316,890 (1982);
U.S. Pat. No. 4,310,518 (1982);
U.S. Pat. No. 4,291,022 (1981);
U.S. Pat. No. 4,238,481 (1980);
U.S. Pat. No. 4,235,886 (1980);
U.S. Pat. No. 4,224,199 (1980);
U.S. Pat. No. 4,211,693 (1980);
U.S. Pat. No. 4,190,648 (1980);
U.S. Pat. No. 4,146,612 (1979);
U.S. Pat. No. 4,133,782 (1979);
U.S. Pat. No. 5,506,339 (1996);
U.S. Pat. No. 4,261,885 (1981);
U.S. Pat. No. 4,728,638 (1988);
U.S. Pat. No. 4,282,143 (1981);
U.S. Pat. No. 4,215,039 (1980);
U.S. Pat. No. 4,209,426 (1980);
U.S. Pat. No. 4,190,575 (1980);
EP Patent No. 0 389 180 (1990);
EP Application No. 0 505 680 (1982);
EP Application No. 0 083 305 (1982);
EP Application No. 0 030 920 (1980);
PCT Application No. WO 88/05052 (1988);
PCT Application No. WO 90/12811 (1990);
PCT Application No. WO 97/01579 (1997);
PCT Application No. WO 91/18016 (1991);
PCT Application No. WO 00/75186 (2000);
U.K. Application No. GB 2,095,261 (1981); and
French Application No. FR 2,522,655 (1983).

Examples of SSTR-1 selective somatostatin agonists include, but are not limited to, the following somatostatin analogs which are disclosed in the above-cited references:
H-Cys-Phe-Phe-D-Trp-Lys-Thr-Phe-Cys-NH$_2$;
and
Caeg-c(D-Cys-Pal-D-Trp-Lys-D-Cys)-Thr(Bzl)-Tyr-NH$_2$, in which the structure for "Caeg" is

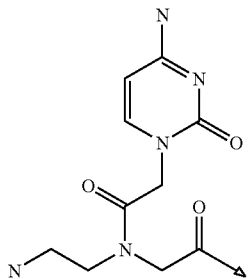

Note that for all somatostatin agonists described herein, each amino acid residue represents the structure of —NH—C(R)H—CO—, in which R is the side chain (e.g., CH$_3$ for Ala). Lines between amino acid residues represent peptide bonds which join the amino acids. Also, where the amino acid residue is optically active, it is the L-form configuration that is intended unless D-form is expressly designated. A disulfide bond (e.g., a disulfide bridge) exists between the two free thiols of the Cys residues; however, it is not shown.

Synthesis of Somatostatin Agonists

The methods for synthesizing somatostatin agonists is well documented and are within the ability of a person of ordinary skill in the art. For example, synthesis of H-D-Phe-Phe-Phe-D-Trp-Lys-Thr-Phe-Thr-NH$_2$, described above, can be achieved by following the protocol set forth in Example I of European Patent Application 0 395 417 A1. The synthesis of somatostatin agonists with a substituted N-terminus can be achieved, for example, by following the protocol set forth in WO 88/02756, European Patent Application No. 0 329 295, and PCT Publication No. WO 94/04752.

Somatostatin Receptor Binding Assays

The human SSTR-1, SSTR-2, SSTR-3, SSTR-4, and SSTR-5 cDNA clones have been described (SSTR-1 and SSTR-2 in Yamada, Y., et al., Proc. Natl. Acad. Sci. USA., 89:251–255 (1992); SSTR-3 in Yamada, et al., Mol. Endocrinol. 6:2136–2142 (1993); and SSTR-4 and SSTR-5 in Yamada, et al., Biochem. Biophys. Res. Commun. 195: 844–852 (1993)) and are also available from American Type Culture Collection (ATCC, Rockville, Md.) (ATCC Nos. 79044 (SSTR-1), 79046 (SSTR-2), and 79048 (SSTR-3)). Based on the restriction endonuclease maps, the entire coding region of each SSTR cDNA may be excised by suitable restriction endonuclease digestion (Maniatis, T., et al., *Molecular Cloning—A Laboratory Manual*, CSHL, 1982). Restriction endonucleases are available from New England Biolabs (Beverly, Mass.). This cDNA fragment was inserted into the mammalian expression vector, pCMV (Russell, D., et al., J. Biol. Chem., 264:8222–8229 (1989)), using standard molecular biology techniques (see e.g., Maniatis, T., et al., Molecular Cloning,—A Laboratory Manual, Cold Spring Harbor Laboratory, 1982) to produce the expression plasmid, pCMV-human SSTR-1 through pCMV-human SSTR-5. Other mammalian expression vectors include pcDNA1/Amp (Invitrogen, Sandlesy, Calif.). The expression plasmids were introduced into the suitable bacterial host, *E. Coli* HB101 (Stratagene, La Jolla, Calif.) and plasmid DNAs, for transfection, were prepared on Cesium Chloride gradients.

CHO-K1 (ovary, Chinese hamster) cells were obtained from ATCC (ATCC No. CCL 61). The cells were grown and maintained in Ham's F12 media (Gibco BRL, Grand Island, N.Y.) supplemented with 10% fetal bovine serum under standard tissue culture conditions. For transfection, the cells were seeded at a density $1 \times 10^6$/60-cm plate (Baxter Scientific Products, McGraw Park, Ill.). DNA mediated transfection was carried out using the calcium phosphate co-precipitation method (Ausubel, F. M., et al., Current Protocols in Molecular Biology, John Wiley & Sons, 1987). The plasmid pRSV-neo (ATCC; ATCC No. 37198) was included as a selectable marker at $\frac{1}{10}$ the concentration of the expression plasmid. CHO-K1 clonal cell lines that have stably inherited the transfected DNA were selected for growth in Ham's F12 media containing 10% fetal bovine serum and 0.5 mg/ml of G418 (Sigma). The cells were ring-cloned and expanded in the same media for analysis.

Expression of the human SSTR-1 through SSTR-5 receptors in the CHO-K1 cells were detected by Northern blot analysis of total RNA prepared from the cells (Sambrook, J. E., et al., Molecular Cloning—A Laboratory Manual, Ed. 2, Cold Spring Harbor Laboratory, Cold Spring Harbor, N.Y., 1989) and by receptor binding using ($^{125}$I-Tyr$^{11}$)somatostatin-14 as a ligand. Transfected cell lines expressing the human SSTR receptors were clonally expanded in culture and used in the following SSTR binding protocol.

Crude membranes were prepared by homogenization of the transfected cells in 20 ml of ice-cold 50 mM Tris-HCl with a POLYTRON homogenizer (setting 6, 15 sec). Buffer was added to obtain a final volume of 40 ml, and the homogenate was centrifuged in a Sorval SS-34 rotor at 39,000 g for 10 min at 0–4° C. The resulting supernatant was decanted and discarded. The pellet was rehomogenized in ice-cold buffer, diluted, and centrifuged as before. The final pellet was resuspended in the 10 mM Tris HCl and held on ice for the receptor binding assay.

Aliquots of the membrane preparation were incubated for 30 min at 30° C. with 0.05 nM ($^{125}$I-Tyr$^{11}$)somatostatin-14 (2000 Ci/mmol; Amersham Corp., Arlington Heights, Ill.) in 50 mM HEPES (pH 7.4) containing a test somatostatin agonist of various concentrations (e.g., $10^{-11}$ to $10^{-6}$), 10 mg/ml bovine serum albumin (fraction V) (Sigma Chemical Co., St. Louis, Mo.), MgCl$_2$ (5 mM), Trasylol (200 KIU ml), bacitracin (0.02 mg/ml), and phenylmethylsulphonyl fluoride (0.02 mg/ml). The final assay volume was 0.3 ml. The incubations were terminated by rapid filtration through GF/C filters (pre-soaked in 0.3% polyethylenimine for 30 min) using a Brandel filtration manifold. Each tube and filter were then washed three times with 5 ml aliquots of ice-cold buffer. Specific binding was defined as the total ($^{125}$I-Tyr$^{11}$) SRIF-14 bound minus that bound in the presence of 1000 nM. The Ki values for somatostatin agonists are calculated by using the following formula: $Ki=IC_{50}/(1+(LC/LEC))$ where $IC_{50}$ is the concentration of test somatostatin agonist required to inhibit 50 percent of the specific binding of the radioligand ($^{125}$I-Tyr$^{11}$)somatostatin-14, LC is the concentration of the radioligand (0.05 nM), and LEC is the equilibrium dissociation constant of the radioligand (0.16 nM).

Inhibition of Proliferation and Capillary Tube Formation

In order to investigate the antiproliferative effects on endothelial cells and the inhibition of proliferation and capillary tube formation of endothelial cells caused by somatostatin analogues, two different human in vitro models have been preformed. These models permitted study of the effects of somatostatin analogues on a bi-dimensional endothelial cell layer and on three-dimensional endothelial cell growth in an extracellular matrix that mimic the capillary development in vivo. Furthermore, these assays allowed a very long period of treatment (72 hours and 28 days, respectively) on human tissues, resembling the possible chronic clinical approach to antiangiogenic therapy.

Material and Methods

Materials

Recombinant human epidermal growth factor (EGF) and recombinant human vascular endothelial growth factor (VEGF) were from PeproTechEC LTD (London, UK). EGF and VEGF, according with the information of data sheet, were reconstituted in sterile distilled water at a concentration of 100 µg/mL.

Cell culture medium 199 and medium 199 without phenol red were purchased from Gibco BRL (Paisley, UK). Type A gelatin from porcine skin supplements and all other chemicals not listed in this section were obtained from Sigma Chemical Co. (St. Louis, Mo., USA). Plastics for cell culture were supplied by Costar (Cambridge, Mass., USA).

Somatostatin-14, BIM-23014C, BIM-23120C, BIM-23190C, BIM-23197C, BIM-23206C, BIM-23268C, BIM-23745C and BIM-23926C (each from Biomeasure, Incorporated, Milford, Mass., USA) were dissolved in a stock solution of 0.01 N acetic acid containing 0.1% fatty acid-free bovine serum albumin (BSA) and stored at −80° C.

The relative affinities of the foregoing compounds for the various somatostatin receptors may be summarized as follows:

| Compound | SSTR-1 | SSTR-2 | SSTR-3 | SSTR-4 | SSTR-5 |
|---|---|---|---|---|---|
| Somatostatin-14 | v. high | v. high | v. high | v. high | v. high |
| BIM-23014C | v. low | v. high | low | v. low | high |
| BIM-23120C | v. low | v. high | v. low | v. low | low |
| BIM-23190C | v. low | v. high | low | v. low | high |
| BIM-23197C | v. low | v. high | mod-high | v. low | high |
| BIM-23206C | v. low | low | v. low | v. low | v. high |
| BIM-23268C | high | mod-high | high | mod-high | v. high |
| BIM-23745C | mod | v. low | v. low | v. low | v. low |
| BIM-23926C | v. high | v. low | v. low | v. low | v. low |

SU5416, 3-((2,4-dimethylpyrrol-5-yl) methylidenyl)-2-indolinone, was a gift from Sugen Inc. (San Francisco, Calif., USA).

Cell Culture Conditions

The immortalized human microvascular endothelial cell line HMEC-1, characterized by Ades, et al., (Journal of Investigative Dermatology 1992, 99: 683–690), was maintained in Medium 199, supplemented with 10% heat-inactivated fetal bovine serum (FBS), penicillin (50 IU/mL) and hydrocortisone (100 µg/mL). Cells were routinely grown in 75 cm2 gelatin-coated tissue culture flasks and kept in a humidified atmosphere of 5% $CO_2$ at 37° C. Cells were harvested with a solution of 0.25% trypsin-0.03% EDTA when they were in long phase of growth and maintained at the above-described culture conditions for all experiments.

Cytotoxicity Assay

In vitro chemosensitivity testing was performed on single-cell suspensions of HEMC-1 cells ($5\times10^3$ cells/well) plated in 96-well gelatin-coated sterile plastic plates and allowed to attach overnight. The treatment protocol (FIG. 1) was designed so that after 24 hours, $10^{-10}$–$10^{-6}$ M somatostatin-14, somatostatin analogues, SU5416 $10^{-6}$ M+VEGF 10 ng/mL as positive control or vehicle were added, and plates were incubated for 72 hours (for more details, see FIG. 1). The treatments were scheduled so that each peptide was represented by at least nine wells. At the end of the experiment, cells were rinsed with phosphate buffered saline (PBS), harvested with trypsin/EDTA, and counted with an hemocytometer. Results are expressed as the percentage of cell proliferation versus controls and are the mean of three separate experiments±S.E repeated thrice.

In vitro Cultures of Human Placental Vessels

The use of the experimental model of human placental explants, detailed below, received authorization by the Ethics committee of Pisa University Hospital (Protocol n. 005567).

Figure 2:
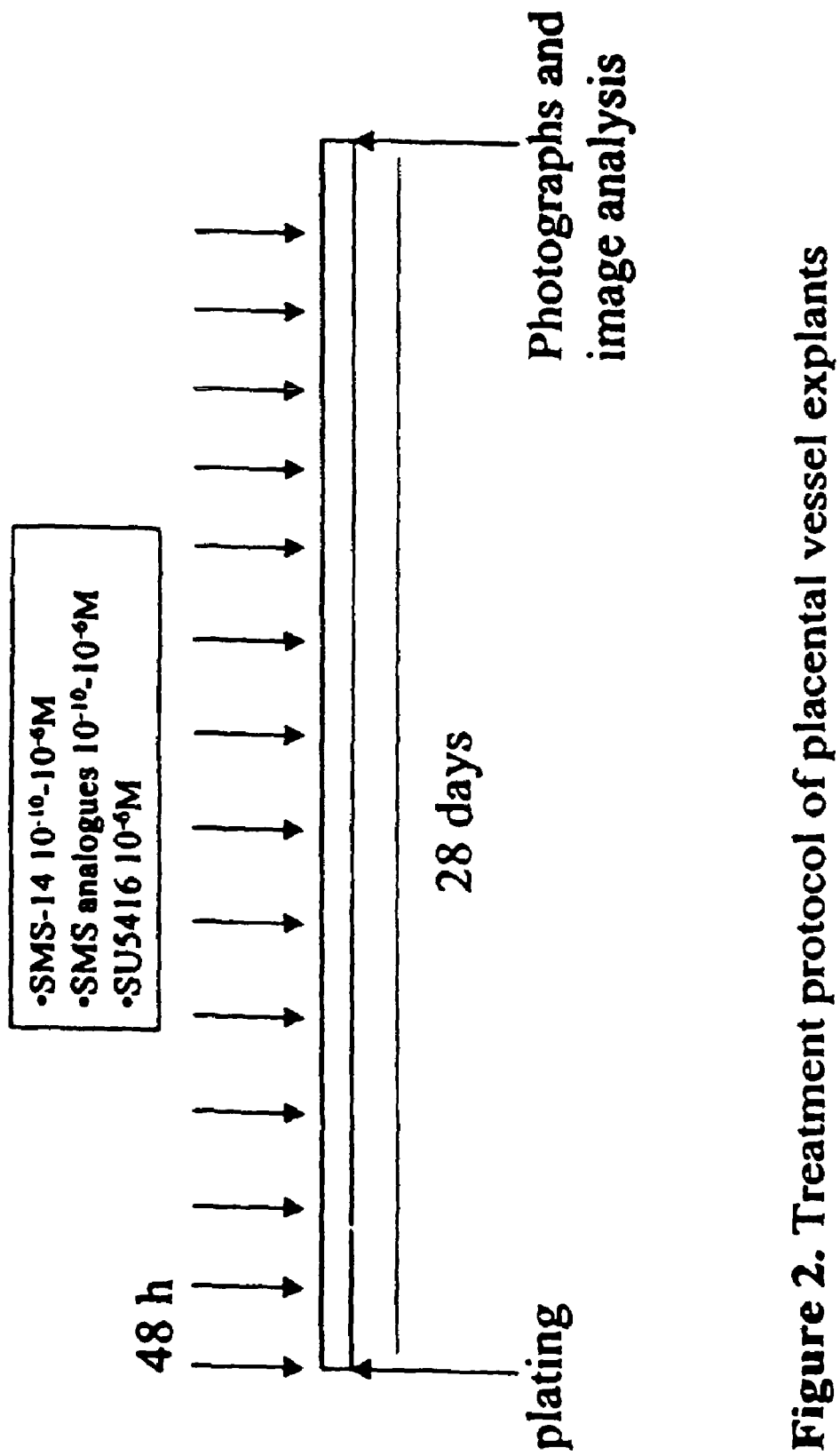
FIG. 2 is a schematic of the treatment protocol of plancental vessel explants as discussed at page 13, line 37 to page 14, line 2.

The experimental procedure described by Brown et al., (Laboratory Investigation 1996, 75: 539–555) was followed and modified in the present study. Immediately after the spontaneous delivery, the placenta was collected in sterile conditions and superficial blood vessels, approximately 1 to 1.5 m in diameter and from 1 to 5 cm in length, were excised. Vessel explants were placed in phosphate buffered saline (PBS) solution containing 2.5 mg/mL of amphotericin B and 50 µg/mL of gentamycin and were cut into approximately 1-mm fragments. The cultures were performed in 24-well culture plates; 0.5 mL/well of a solution of fibrinogen 3 mg/mL in Medium 199 without phenol red was added to each well followed by the quick addition of 15 µL of thrombin (50 NIH U/mL in 0.15 M NaCl). The vessel explants were rapidly placed in the center of the wells after clot formation and covered by 0.5 mL/well of the fibrinogen solution with the addition of further 15 µL of thrombin for suspending all of them at the same level between the two clots. After gel formation, 1 mL/well of medium 199 without phenol red supplemented with 10% of heat-inactivated FBS, 0.1% ε-aminocaproic acid, L-glutamine (2 mM), and antibiotics (streptomycin 50 µg/mL, penicillin 50 IU/mL and amphotericin B 2.5 mg/mL) were added. Vessels were cultured and treated every two days with $10^{-10}$–$10^{-6}$ M somatostatin-14, somatostatin analogues, and SU5416 $10^{-6}$ M or vehicle at 37° C. 95% air/5% $CO_2$ in a humidified environment for 28 days (FIG. 2). Vessels explants were photographed on day 28 with a phase-contrast Leitz MD IL microscope (Leica, Heerbrugg, Switzerland) and were subjected to image analysis.

Image Analysis

The image analysis procedures described by Bocci et al., (Cancer Chemotherapy Pharmacology 1999, 43: 205–212), were adopted for the present study. Briefly, photographs obtained from the placental fragment assay were digitized in a 512×512-pixel matrix, using a color video camera TK-1280E (JVC, Tokyo, Japan) and a microcomputer processor. Digitized pictures were visualized on highresolution color display. The true color image analysis software package KS 300 v.1.2 (Kontron Elektronik GmbH, Eching, Germany) was run for interactive manipulation, quantification of the images and data collection. Geometric calibrations were set with a sample of known dimensions and agray-scale analysis was performed to measure the density of the image that was in the range of 0–255, where 0 was black (presence of vascular sprouts) and 255 was white (absence of vascular sprouts). In the fibrin culture of placental vessel explants the mean gray level of the sprouting area was measured and the sprouting index (SI) was defined as:

Sprouting index=((sprouting area/mean gray level of sprouting area)/perimeter of explant)×100.

Results are expressed as the percentage of sprouting index+/–S.E. versus controls.

Results

Cytotoxicity Assay

All results are shown in Table I. All somatostatin analogues at the studies concentrations revealed antiproliferative activity on immortalized human microvascular endothelial HMEC-1 cells, with a maximum effect at $10^{-7}$–$10^{-8}$ M. The positive control of SU5416 $10^{-6}$ M, a specific VEGF-receptor inhibitor, resulted in a cell growth block of 56.2%.

In vitro Cultures of Human Placental Vessels

Figure 3:
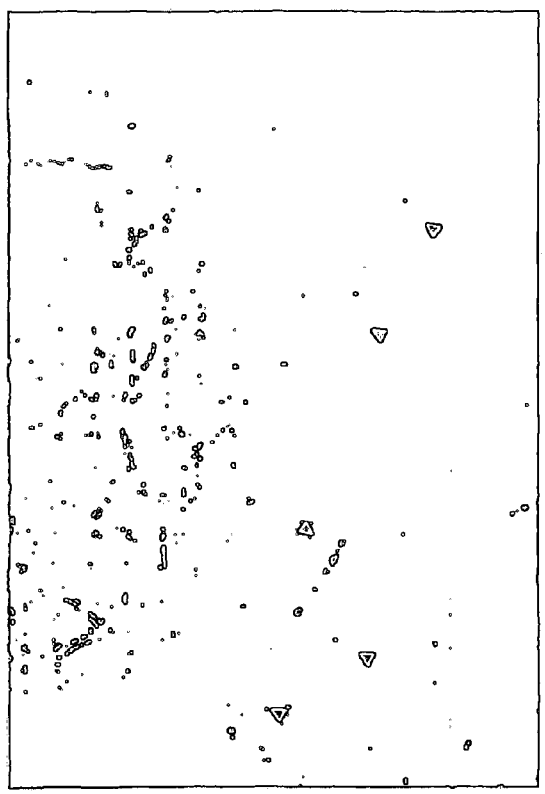
FIG. 3 shows a view of vascular cells organized radially to form microvessels that underwent continuous remodeling.
Figure 5:
FIGS. 4 and 5 show a framework of endothelial cells that were immunoreactive for von Willebrand factor.
Figure 4:
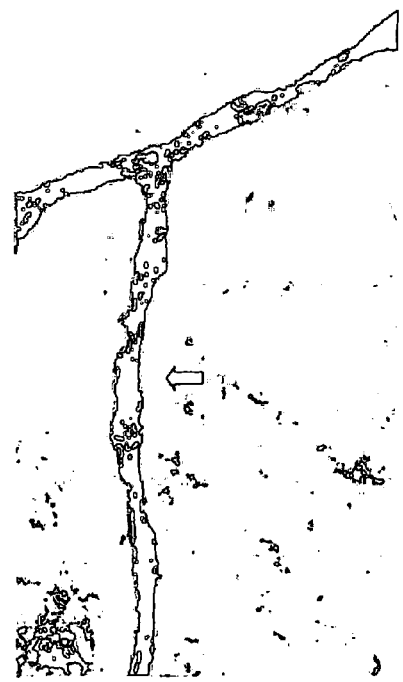

The explant sprouting within the fibrin matrix was characterized by numerous microvessels around the placental fragment. Vascular cells organized radially to form microvessels that underwent continuous remodeling (FIG. 3). The maximal growth of the three-dimensional microvascular network occurred during the third-fourth week and reached the plateau at 27 days after explant. Histologically, in the fibrin gel a subtle framework of endothelial cells, that was immunoreactive for von Willebrand factor (FIG. 4), was observed (FIG. 5). In most of the cases the microvessels showed an initial lumen; in other the lumen was absent and only endothelial cells were observed (FIG. 5).

Figure 6:
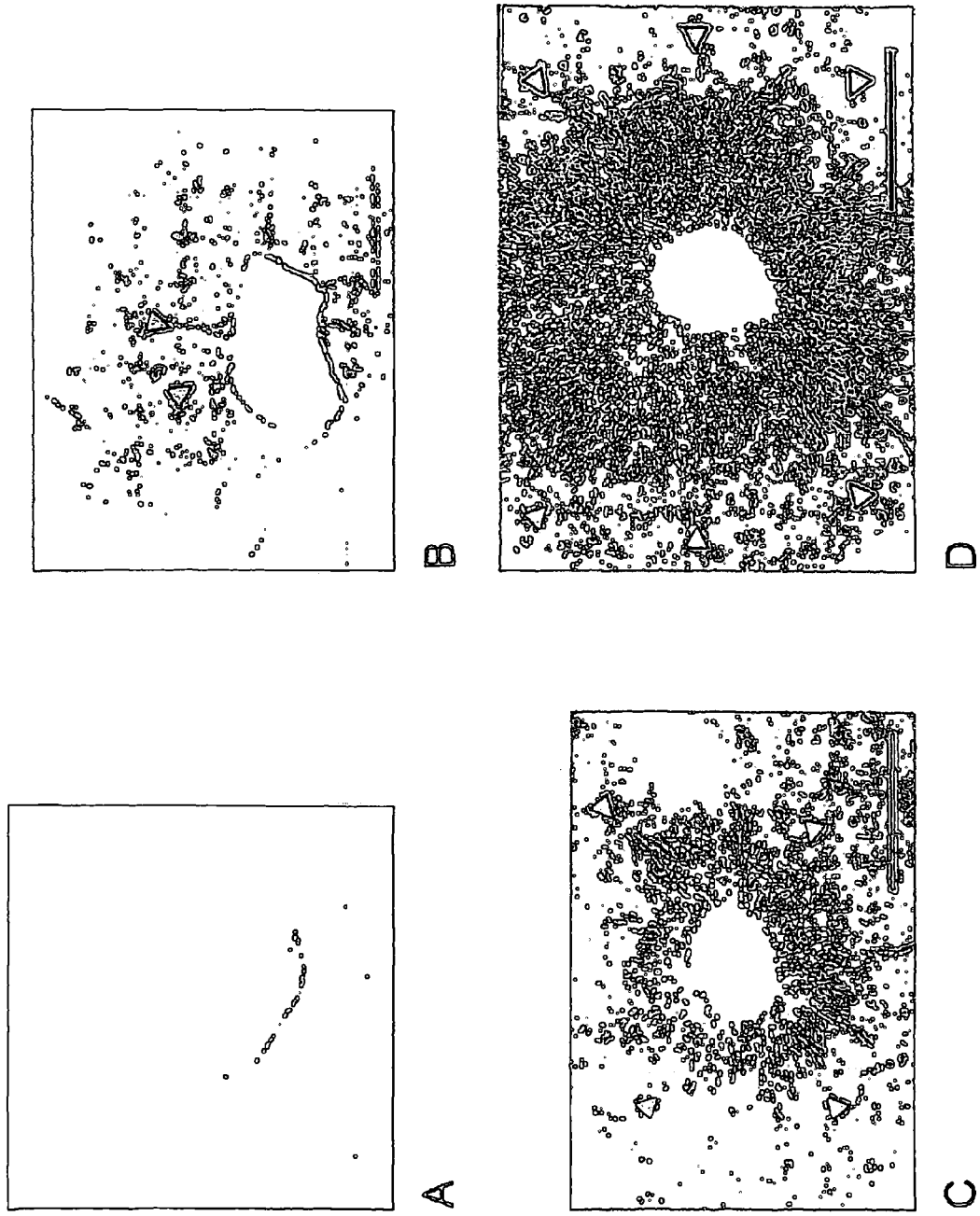
FIG. 6 shows a series of microscopic pictures of placental explants on the first day of culture.

The microscopic picture of the placental explants on the first day of the culture is shown in FIG. 6A (bar, 2 mm); the appearance of the outgrowth of endothelial cells from the placental cultured vessel fragment was observed approximately on the sixth day of culture (SI=0.055±0.004 (mm/mean gray)×100; FIG. 6D).

The experimental data on the activity of somatostatin analogues on capillaries sprouts were summarized in Table II. Cultures treated with SMS analogues and SU5416 were shown in FIGS. 7–16 where the maximum effects were shown. BIM-23926C and BIM-23745C revealed a potent inhibitory property in a long-term treatment; they resulted, respectively, in 17.18±11.8% at $10^{-7}$ M and 42.84±5.6% at $10^{-8}$ M of SI as compared to untreated controls. SU5416, the positive control, resulted in 32.92±9.7% of SI at a concentration of $10^{-6}$ M.

OTHER EMBODIMENTS

The foregoing description has been limited to specific embodiments of this invention. It will be apparent, however, that variations and modifications may be made to the invention, with the attainment of some or all of the advantages of the invention. Such embodiments are also within the scope of the following claims.

What is claimed is:

1. A method of treating vascular proliferation in a patient, said method comprising administering a therapeutically effective amount of a somatostatin type-1 receptor agonist to said patient wherein said somatostatin type-1 receptor agonist is a somatostatin type-1 receptor selective agonist having a Ki for the somatostatin type-1 receptor which is less than 5 nM and at least 10 times less than the Ki for said somatostatin type-1 receptor agonist for each of the somatostatin type-2, type-3, type-4, and type-5 receptors provided that said somatostatin type-1 receptor agonist is not H-D-Phe-Phe-Phe-D-Trp-Lys-Thr-Phe-Thr-$NH_2$ or 3-((2,4-dimethylpyrrol-5-yl) methylidenyl)-2-indolinone.

2. The method according to claim 1 wherein the somatostatin type-1 receptor selective agonist is Caeg-c(D-Cys-Pal-D-Trp-Lys-D-Cys)-Thr(Bzl)-Tyr-$NH_2$ or a pharmaceutically acceptable salt thereof.

3. The method of claim 1, wherein said vascular proliferation comprises angiogenesis, restenosis, endothelial cell proliferation, smooth muscle proliferation, or new blood vessel sprouting.

4. The method of claim 1, wherein said vascular proliferation occurs in a disease or condition comprising an autoimmune disease, arthritis, scleroderma, cancerous tumors, corneal graft neovascularization, diabetic retinopathy, hemangioma, hypertrophic scarring, or psoriasis.

5. The method of claim 1, wherein said vascular proliferation is incident to or associated with angioplasty or an AV shunt.

6. The method of claim 1, wherein said vascular proliferation occurs in a disease or condition comprising warts, granulomas, Kaposi's sarcoma, or allergic oedema.

7. The method of claim 1, wherein said vascular proliferation occurs in a disease or condition comprising endometriosis, dysfunctional uterine bleeding, or follicular cysts.

8. The method of claim 1, wherein said vascular proliferation occurs in a disease or condition comprising retinopathy of prematurity, choroidopathy, macular degeneration, or age-related macular degeneration.

9. The method of claim 1, wherein said vascular proliferation occurs in a disease or condition comprising solid tumor, tumor metastasis, benign tumor, acoustic neuromas, neurofibromas, trachomas, leukemia, pyogenic granuloma, myocardial angiogenesis, plaque neovascularization, atherosclerosis, coronary collaterals, cerebral collaterals, arteriovenous malformations, ischemic limb angiogenesis, corneal graft rejection, Osler-Webber Syndrome, rubeosis, neovascular glaucoma, retrolental fibroplasia, diabetic retinopathy, diabetic neovascularization, fracture, vasculogenesis, hematopoiesis, ovulation, menstruation, placentation, cat scratch disease (Rochele minalia quintosa), peptic ulcer, *Helicobacter pylori* associated ulcer, psoriasis, telangiectasia psoriasis, rheumatoid arthritis, Crohn's disease, intestinal adhesions, scarring, hypertrophic scars, keloids, telangiectasia, hemophiliac joints, angiofibroma, or wound granulation.

10. The method of claim 1, wherein said somatostatin type-1 receptor agonist is disposed upon or within a vascular stent.

11. The method of claim 10, wherein said somatostatin type-1 receptor agonist is provided as a component of a slow release formulation.

12. The method of claim 10, wherein said somatostatin type-1 receptor agonist is provided as a component of a polymeric composition.

* * * * *